United States Patent [19]
Feldman

[11] Patent Number: 5,788,643
[45] Date of Patent: Aug. 4, 1998

[54] PROCESS FOR MONITORING PATIENTS WITH CHRONIC CONGESTIVE HEART FAILURE

[75] Inventor: Charles L. Feldman, Framingham, Mass.

[73] Assignee: Zymed Medical Instrumentation, Inc., Camarillo, Calif.

[21] Appl. No.: 837,901

[22] Filed: Apr. 22, 1997

[51] Int. Cl.$^6$ ............................................ A61B 5/02
[52] U.S. Cl. .................. 600/506; 600/547; 600/481; 128/898
[58] Field of Search .................... 600/301, 305, 600/345, 382, 384, 547, 561, 481, 483, 506; 128/898

[56] References Cited

U.S. PATENT DOCUMENTS

| | | | |
|---|---|---|---|
| 4,008,712 | 2/1977 | Nyboer | 128/734 |
| 4,197,845 | 4/1980 | Kasa | 128/630 |
| 4,793,362 | 12/1988 | Tedner | 128/734 |
| 4,803,625 | 2/1989 | Fu et al. | |
| 4,895,163 | 1/1990 | Libke et al. | 128/734 |
| 4,911,175 | 3/1990 | Shizgal | 128/734 |
| 4,947,862 | 8/1990 | Kelly | 128/734 |
| 5,086,781 | 2/1992 | Bookspan | 128/734 |
| 5,203,344 | 4/1993 | Scheltinga et al. | 128/734 |
| 5,282,840 | 2/1994 | Hudrlik | 128/734 |
| 5,335,667 | 8/1994 | Cha et al. | 128/734 |
| 5,372,141 | 12/1994 | Gallup et al. | 128/734 |
| 5,396,886 | 3/1995 | Cuypers | 128/630 |
| 5,415,176 | 5/1995 | Sato et al. | 128/734 |
| 5,427,113 | 6/1995 | Hiroshi et al. | 128/734 |
| 5,449,000 | 9/1995 | Libke et al. | 128/734 |
| 5,482,035 | 1/1996 | Paloheimo | 128/630 |
| 5,529,072 | 6/1996 | Sramek | 128/693 |
| 5,579,782 | 12/1996 | Masuo | 128/734 |
| 5,584,291 | 12/1996 | Vapola et al. | 128/630 |
| 5,611,351 | 3/1997 | Sato et al. | 128/734 |
| 5,615,689 | 4/1997 | Kotler | 128/734 |

OTHER PUBLICATIONS

Transthoracic Bioelectrical Impedance Analysis in Normal Adults (Abstract), Maissonneuve Rosemont Hospital Research Ctr, Nierman et al, Mt. Sinai Med. Ctr., p. A331.
RJL Systems, Inc. Bioelectrical Impedance Users Manual, Sep. 15, 1989.
Estimation of Body Fluid Volumes Using Tetrapolar Bioelectrical Impedance Measurements, Henry C. Lukaski and William W. Bolonchuk, Aviation Space and Environmental Medicine, 1988, pp. 1163–1169.
Total Body Water in Congestive Heart Failure A Pre and Post Treatment Study by R. Subramanyan, et al., Jr. Asso. Phys. Ind., vol. 28, Sep., 1980, pp. 257–262.
Bioimpedance Analysis, For a Better Quality of Life, by Rudolph J. Liedtke, President RJL Systems, 4 pages.
Nutritional Assessment with Bioelectrical Impedance Analysis in Maintenance Hemodialysis Patients[1,2] by Blenn M. Chertow, et al., vol. 6, No. 1, 1995, pp. 75–81.
Accuracy of Bioelectrical Impedance Analysis in Estimation of Extracellular Space in Healthy Subjects and in Fluid Retention States, Ann Nutr Metab 1994; 38:158–165.
Your Invitation to Fluid & Nutrition Analysis, RJL Systems, 24 pages.

*Primary Examiner*—Kimberly L. Asher
*Attorney, Agent, or Firm*—Kelly Bauersfeld Lowry & Kelley, LLP

[57] ABSTRACT

In a process for monitoring patients with chronic congestive heart failure, a high frequency current is passed between electrodes applied to two limbs of a patient. The current, voltage and phase angle between the measured current and voltage are measured to enable the calculation of congestive heart failure (CHF) indicia values. The calculated CHF indicia values are then compared with baseline values established when the patient is in a known, stable condition. Intervention is initiated if the differences between the calculated CHF indicia values and the baseline values are outside of established tolerances. The CHF indicia values may include resistance, reactance, impedance, total body water and extracellular water. Moreover, the CHF indicia values may include a figure of merit indicative of the hydration status of the patient.

36 Claims, 2 Drawing Sheets

PROCESS FOR MONITORING PATIENTS WITH CHRONIC CONGESTIVE HEART FAILURE

BACKGROUND OF THE INVENTION

Congestive heart failure (CHF) results when the heart is unable to contract with sufficient vigor to meet the body's need for oxygen. Under such circumstances, to increase cardiac output, autoregulatory mechanisms allow the filling pressure in the ventricles to increase, thus elongating myocardial fibers at the start of systole and increasing the strength of contraction. When the left and/or right filling pressures exceed approximately 15 mm Hg, blood components are forced out of the vasculature and into the interstitium, resulting in pulmonary edema (left heart failure) and/or peripheral edema and ascites (right heart failure). The end results is severe incapacitation and possibly death.

In a portion of the population with heart disease of many different etiologies—approximately 600,000 members of the U.S. population—the ability of the heart to meet the body's needs is marginal, resulting in chronic heart failure. For these patients, most of whom can be stabilized by medication and dietary restrictions and many of whom are quite elderly, minor variations in physical activity, emotional stress or non-compliance with diet or medication regimes can result in destabilization and episodes of acute heart failure requiring urgent hospitalization. Indeed, hospitalization for heart failure is the second most costly admitting diagnosis of the Medicare program.

The most reliable existing method to monitor CHF is by direct measurement of pulmonary artery and central venous pressures through catheters inserted into the bloodstream. This method, though highly accurate, is clearly impractical outside of a hospital setting. Other methods include observation of the arterial pressure pattern (invasively or noninvasively) during a Valsalva maneuver, measurement of flow though the mitral annulus and in the pulmonary veins using doppler echocardiography, observation of neck vein distension, measurement of ankle dimensions and careful tracking of body weight. The first two, though reasonably accurate, require considerable equipment and trained personnel while the last three are quite unreliable for a variety of reasons.

Subramanyan, et al. and others have shown that both the resistive and reactive components of the body's impedance to the flow of relatively high frequency (50 kHz) electrical current is sensitive to the amount of fluid retained by a patient with CHF. As the CHF resolves, resistance and reactance both increase as does the electrical phase angle ($\tan^{-1}$reactance/resistance). See Subramanyan, et al., *Total Body Water in Congestive Heart Failure*, Jour. Asso. Phys. Ind., Vol.28, September, 1980, pages 257–262. Others, including Lukaski & Bolonchuk, have derived relationships between the components of the body's electrical impedance at either 50 kHz or 1000 Hz and either total body water or extracellular fluid. See Lukaski, et al., *Estimation of Body Fluid Volumes Using Tetrapolar Bioelectrical Impedance Measurements*, Aviation Space and Environmental Medicine; 1988; 59: 1163–1169.

There remains a need, however, for a practical and reliable method for monitoring the status of CHF patients outside of a hospital setting. Such a monitoring method may build on the observations of Subramanyan et al. and Lukaski & Bolonchuk with the goal of intervening before the onset of acute CHF. It would be most desirable to provide a simple way of detecting increases in body water of patients with CHF before hospitalization is necessary and permitting adjustments in medication and/or diet in time to prevent an episode of acute heart failure. The present invention fulfills these needs and provides other related advantages.

SUMMARY OF THE INVENTION

The present invention resides in an "early warning" monitoring system for determining changes in the status of patients with chronic congestive heart failure (CHF), with the goal of intervening before the onset of acute congestive heart failure. In accordance with the present invention, a process for monitoring patients with chronic congestive heart failure comprises the steps of applying electrodes to two points on the body, passing a current at one or more high frequencies between the electrodes, and then measuring the current (I) and voltage (V). Congestive heart failure (CHF) indicia values are calculated based on the measured current (I) and voltage (V), and the calculated CHF indicia values are then compared with baseline values established when the patient is in a known, stable condition, to determine if differences therebetween are within established tolerances.

In a preferred form of the invention the process comprises the steps of applying the electrodes to two limbs of a patient and then passing a high frequency current between the electrodes. Current (I), voltage (V) and phase angle ($\phi$) are measured, and then congestive heart failure (CHF) indicia values, including resistance (R) and reactance ($Z_c$), are calculated. The calculated CHF indicia values are then compared with baseline values, and intervention is initiated when the differences between the calculated CHF indicia values and the baseline values are outside of established tolerances. The process is repeated at an interval determined by whether or not intervention was required. The calculated CHF indicia values may include, in addition, impedance (Z).

A decrease in the phase angle ($\phi$) or any of the calculated CHF indicia values of resistance (R), reactance ($Z_c$) or impedance (Z), is an indicator of the need to initiate intervention. The tolerances from baseline values for the calculated CHF indicia values are on the order of five percent (5%) for resistance (R) and impedance (Z), ten percent (10%) for reactance ($Z_c$), and twenty percent (20%) for phase angle ($\phi$).

The calculated CHF indicia values may also include total body water (TBW) and extracellular water (ECW). An increase in the calculated total body water (TBW) or extracellular water (ECW) is an indicator of the need to initiate intervention. The tolerances from baseline values are on the order of five percent (5%) for total body water (TBW) and extracellular water (ECW). Total body water (TBW) may be calculated utilizing the formula:

$$TBW = 0.377\ Ht^2/R + 0.14\ Wt - 0.08\ Age + 2.9\ Gender + 4.65\ (\text{Where Gender} = 1\ \text{for male and 0 for female}).$$

Extracellular water (ECW) may be calculated utilizing the formula:

$$ECW = 0.189\ Ht^2/R + 0.52\ Wt - 0.0002\ Ht^2/Z_c + 1.03.$$

The calculated CHF indicia values may further include a figure of merit which is indicative of the hydration status of the patient. By way of example, the figure of merit may be derived from the ratio of extracellular water (ECW) over fat-free mass (FFM). Fat-free mass (FFM) may be calculated utilizing the formula:

$FFM = -15.26 - 0.775\ (Ht^2/R) + 0.146\ Wt + 0.185\ Z_c$.

Intervention is indicated when the ratio of extracellular water (ECW) to fat-free mass (FFM) is greater than approximately 0.30. Moreover, an increase in the figure of merit on the order of one percent (1%) is an additional indicator of the need to initiate intervention.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
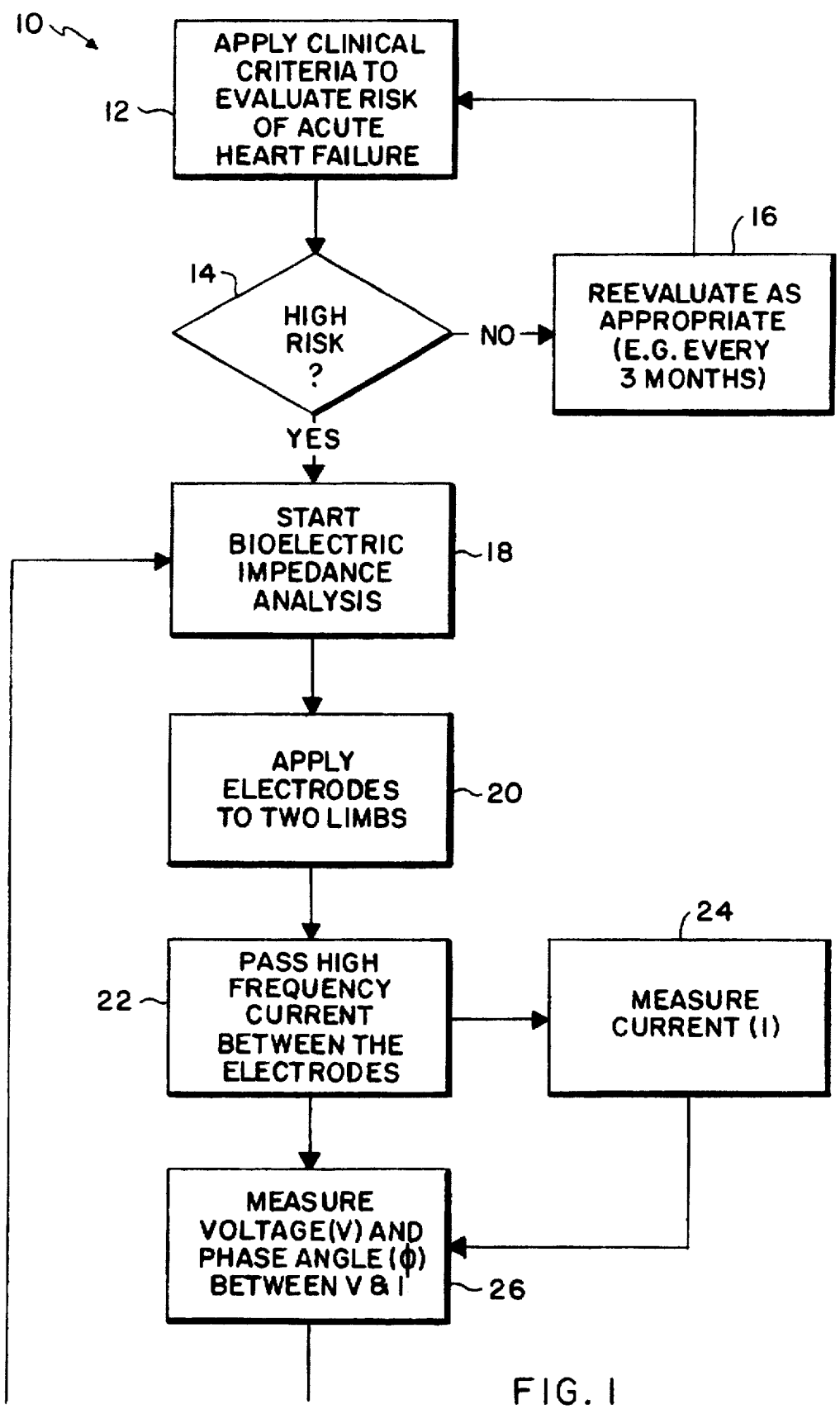
FIG. 1 is the first of a two-part flow chart illustrating a process for monitoring patients with chronic congestive heart failure embodying the present invention.
Figure 2:
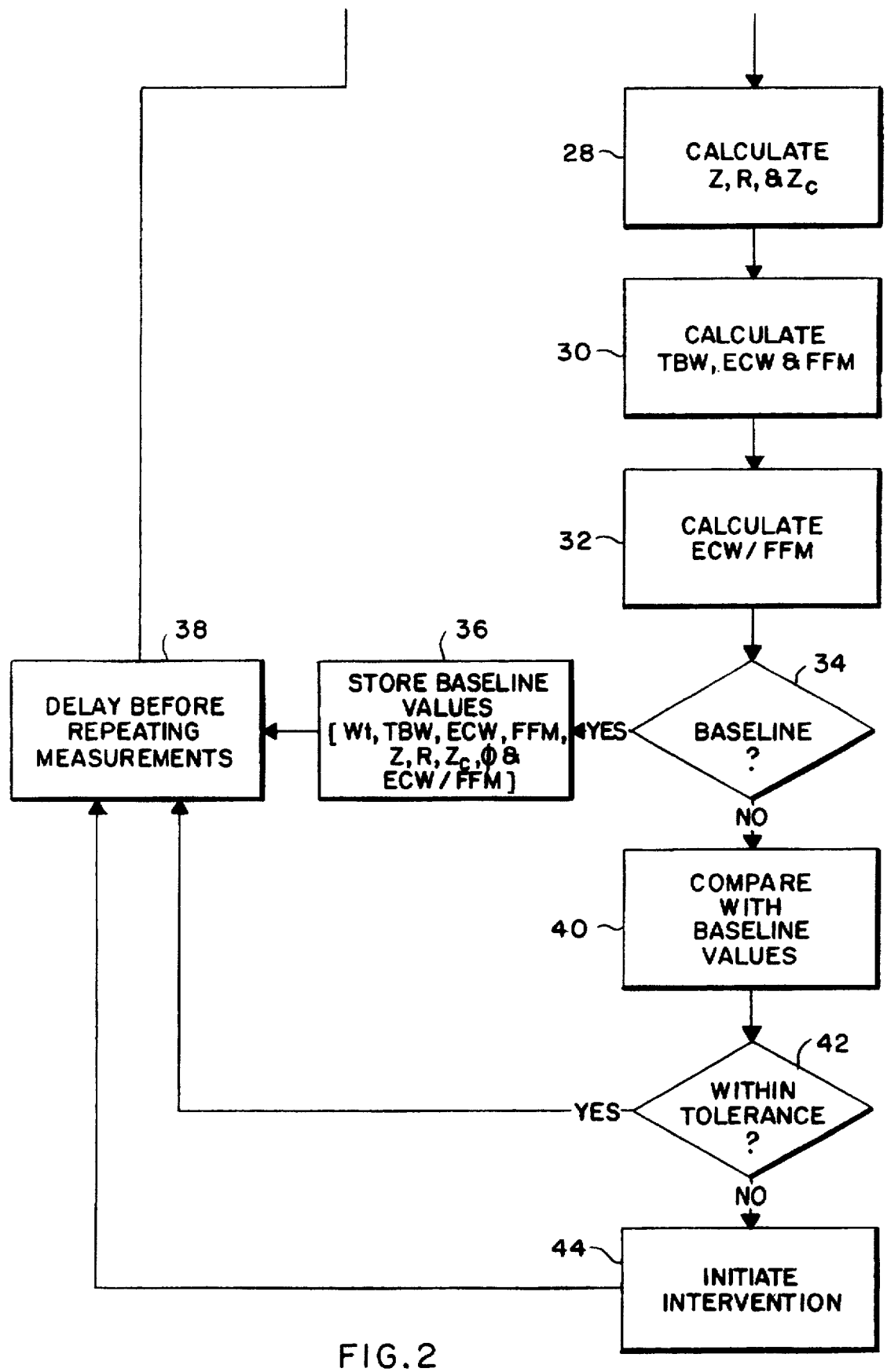
FIG. 2 is the second of the two-part flow chart illustrating the process of the present invention.

As shown in the drawings for purposes of illustration, the present invention is concerned with a novel process for monitoring patients with congestive heart failure, generally indicated in FIGS. 1 and 2 by the reference number 10. In accordance with the present invention, the process 10 comprises, generally, the steps of applying electrodes to two points on the body of a patient and, while passing a current at one or more high frequencies between the electrodes, measuring the current (I) and voltage (V). Congestive heart failure (CHF) indicia values are then calculated based on the measured current (I) and voltage (V), which are compared with baseline values to determine if differences therebetween are within established tolerances. If those differences are outside of the established tolerances, intervention is initiated in accordance with sound medical practice. Thus, the process 10 of the present invention provides an "early warning" monitoring system for determining changes in the status of patients with chronic congestive heart failure with the goal of intervening before the onset of acute CHF.

The process 10 of the present invention involves the tracking of total body impedance (Z), resistance (R), reactance ($Z_c$) and phase angle ($\phi$) in an abulatory patient with chronic congestive heart failure (CHF), and uses the decrease of any or all of these "indicia values" as predictors of the onset of acute CHF. The measurement can be made using a commercial device, such as that manufactured by RJL Systems of Clinton Twp., Mich., to measure body composition, or a similar device designed for this purpose. Significant intra-patient changes over time in the values of these parameters (for example five percent or more) would be viewed as indicators of a deteriorating physical condition. The electrodes may be placed on any two points on the body, but preferably are positioned on either the ipsilateral wrist and ankle or on the contralateral wrist and ankle as described in Subramanyan, et al., *Total Body Water in Congestive Heart Failure*, Jour. Asso. Phys. Ind., Vol. 28, September, 1980, pages 257–262. Measurements are typically made at a high frequency (above 20 kHz—largely sensitive to total body water, or below 20 kHz—sensitive primarily to volume of extracellular fluid), or multiple frequencies.

The process 10 of the present invention also includes utilizing the techniques described above applied to separate portions of the body of the patient to separately track peripheral and pulmonary edema. For example, measuring and tracking ankle-to-ankle impedance (Z) and its components would highlight changes in peripheral fluid, primarily indicative of right heart failure. Wrist-to-wrist impedance (Z) components would be more indicative of changes in lung fluid and left heart failure. Changes in any of these component impedance values would be used as an indicator of instability and suggest changes in therapeutic regimen.

Combining the measurements obtained above with body dimensions and body weight in formulas such as those described by Lukaski, H. C. & Bolonchuk, W. W. *Estimation of Body Fluid Volumes Using Tetrapolar Bioelectrical Impedance Measurements*, Aviation Space and Environmental Medicine; 1988; 59; 1163–1169 enables estimates to be obtained of total body water (TBW) and intracellular and extracellular water (ECW). Increases in the estimated amount of total or extracellular water of approximately one half to one liter from its baseline value would be used as an indicator progressive heart failure and for therapeutic intervention. Moreover, combining estimates of total and extracellular water with estimates of body cell mass into a "figure of merit" indicative of the hydration status of the patient may be advantageously accomplished in accordance with the process 10 of the present invention. Changes in the "figure of merit" would be used as an indicator of worsening condition of the CHF patient. Typical figures of merit would include the ratio of extracellular fluid (ECW)/fat-free mass (FFM), or the ratio of extracellular water (ECW)/total body weight. An increases in the figure of merit of approximately one percent (1%) would be used as an indicator of worsening condition. Moreover, certain figures of merit, per se, rather than their change may be utilized as an indicator of congestive heart failure. For example, when the ratio of extracellular water (ECW)/fat-free mass (FFM) is greater than approximately 0.30, it may be assumed that the patient is in congestive heart failure.

With reference specifically to FIG. 1, the process 10 begins by applying clinical criteria to evaluate the risk of acute heart failure (block 12). Factors to be evaluated are the patient's history of hospitalization for congestive heart failure (CHF), left ventricular ejection fraction (EF—the fraction of the left ventricle that is emptied in each cardiac contraction), and typical signs of CHF including neck vein distention, shortness of breath and swelling of the extremities. The patient is next evaluated to determine whether or not he or she may be classified as a high risk (block 14). High risk patients are those who have been hospitalized for CHF within the last three months, those who have been hospitalized for CHF within the last year and show new neck vein distention, those who have shortness of breath at rest or with minimal exertion, and/or those with an ejection fraction (EF) less than forty percent, for example. If the patient is not classified as a high risk, the physician may reevaluate the diagnosis as appropriate, for example, every three months or so (block 16). If, on the other hand, the patient is evaluated to be a high risk, then the bioelectric impedance analysis of the present invention is conducted to enable the health care provider to determine the patient's congestive heart failure (CHF) indicia values for purposes of comparing those values with baseline values established when the patient is in a known stable condition (block 18).

In the preferred embodiment, two electrodes are attached to each of two limbs (block 20). The two more distal electrodes (i.e., hand and foot) are used for injecting current (I) while the two more proximal electrodes (i.e., wrist and ankle) are used for measuring voltage (V). If, however, the electrodes have sufficient surface area so that the contact impedance is very low compared to the impedance (Z) of the body (i.e., <<500Ω), a single electrode on each of the two limbs can be used for both current injection and voltage measurement. Any pair of limbs may be used (right arm to left leg, right arm to left arm, etc.), or multiple pairs can be used and results calculated pair-by-pair. In the preferred embodiment, the electrodes are attached to the lower left extremity and the upper right extremity.

Once the electrodes have been properly attached to the patient, a high frequency current is passed between the electrodes (block 22). A typical (preferred) current is 800 μamp at 50 kHz. A current of up to 5 ma could be used as well as any single frequency from 10 kHz to 100 kHz. Alternatively, two different frequencies, one below 10 kHz (for example 1 kHz) and one above (for example 100 kHz) could be utilized. As the high frequency current is passed between the electrodes, the current (I) is measured (block 24) as well as the voltage (V) and phase angle ($\phi$) between the measured current (I) and voltage (V) (block 26). In this regard, the voltage (V) and current (I) can be measured with any conventional technique, analog or digital. As is known by those in the art, the delay between voltage and current in zero crossing (current lags voltage) bears the same relation to the waveform period as the phase angle ($\phi$) does to 360°. In other words, the phase angle ($\phi$)=360($t_d$), where $t_d$ is the time by which current (I) lags voltage (V), and (T) is the waveform period (the inverse of frequency). For a 50 kHz current, T=1/50,000=20μ seconds.

Having thus measured the current (I), voltage (V) and the phase angle ($\phi$), congestive heart failure (CHF) indicia values may then be calculated (blocks 28, 30 and 32). As illustrated in block 28, the first indicia values calculated include impedance (Z), resistance (R) and reactance ($Z_c$). Impedance (Z) is the rms voltage divided rms current. Resistance (R) is the impedance (Z) multiplied by the cosine of the phase angle ($\phi$), or R=Z cos $\phi$. Reactance ($Z_c$) is the capacitive component of impedance (Z) and is determined by multiplying the impedance (Z) by the sine of the phase angle ($\phi$), or $Z_c$=Z sin $\phi$.

As illustrated in block 30, the patient's total body water (TBW), extracellular water (ECW) and fat-free mass (FFM) may also be calculated to provide CHF indicia values. Total body water (TBW) and extracellular water (ECW) can be calculated from the formulas of Lukaski H. C. & Bolonchuk W. W. *Estimation of Body Fluid Volumes Using Tetrapolar Bioelectrical Impedance Measurements.* Aviation Space and Environmental Medicine, 1988; 59; 1163–1169. These formulas are:

$$TBW=0.377\ Ht^2/R+0.14\ Wt-0.08\ Age+2.9\ Gender+4.65\ (\text{Where Gender}=1\ \text{for male and 0 for female}),\ \text{and}$$

$$ECW=0.189\ Ht^2/R+0.52\ Wt-0.0002\ Ht^2/Z_c+1.03$$

wherein Ht=the height of the patient (cm) and Wt=the weight of the patient (Kg). Fat-free mass (FFM) can be calculated from the formula provided in Huges, V. A., and Evans W. J. *Assessment of Fat-Free Mass in an Older Population Using Bioelectric Impedance.* Fed Proc 1987; 46 (Abstract), as follows:

$$FFM=-15.26-0.775\ (Ht^2/R)+0.146\ Wt+0.185\ Z_c$$

Other versions of these formulas are available as are formulae for two frequency analyses.

Block 32 illustrates deriving a "figure of merit" from the ratio of extracellular water (ECW) over fat-free mass (FFM).

When beginning the monitoring program, it is necessary to establish baseline values for the calculated CHF indicia (blocks 28–32). The baseline values are preferably measured when the patient is in a known, stable condition, such as when discharged from the hospital and/or entered into the monitoring program. If it is the baseline values that are being established (block 34), they are stored (block 36) for further reference. The stored baseline values will typically include the weight (Wt) of the patient, the calculated impedance (Z), resistance (R), reactance ($Z_c$), phase angle ($\phi$), total body water (TBW), extracellular water (ECW), fat-free mass (FFM), and the ratio of extracellular water to fat-free mass (ECW/FFM). Once the baseline values have been established and stored (block 36), there is a delay (block 38) before repeating the bioelectric impedance analysis (18). The preferred delay before repeating the measurements is one to two weeks.

Subsequent analyses (18) follow the same process steps 20–32 as discussed above. However, since the baseline values have already been established and stored (34, 36) the newly calculated indicia values (28, 30 and 32) are then compared with the previously established baseline values (block 40) to determine if differences therebetween are within established tolerances (block 42). In the preferred embodiment of the invention, a decrease in the phase angle ($\phi$) or any of the calculated CHF indicia values of resistance (R), reactance ($Z_c$) or impedance (Z), is an indicator of the need to initiate intervention. The tolerances from baseline values are on the order of five percent (5%) for resistance (R) and impedance (Z), ten percent (10%) for reactance ($Z_c$), and twenty percent (20%) for phase angle ($\phi$). An increase in the calculated total body water (TBW) or extracellular water (ECW) is an indicator of the need to initiate intervention. The tolerances from baseline values for such calculated CHF indicia values are on the order of five percent (5%) for both the total body water (TBW) and extracellular water (ECW) calculations. With regard to the figure of merit derived from the ratio of extracellular water (ECW) over fat-free mass (FFM), intervention is indicated when such ratio is greater than approximately 0.30 and/or there is an increase in the figure of merit on the order of one percent (1%).

If the calculated CHF indicia values are within established tolerances, then there is simply a delay (38) before repeating measurements. In particular, for those patients these measurements fall within tolerances, the preferred delay before repeating the measurements is one to two weeks. Patients whose clinical history so indicated could be monitored either less frequently or more frequently.

For those patients whose measurements do not fall within tolerances, intervention is indicated (block 44). Interventions are based on medical judgment and form no part of the present invention. They might include counseling to reduce the amount of salt in the diet or reduce activity. The use of diuretics and/or angiotensin converting enzyme inhibitors could be increased. In severe cases, intravenous diuretics could be started as could intravenous agents to increase the pumping action of the heart (inotropes such as dobutamine), or the patient could be advised to seek hospitalization. Patients undergoing stabilization through therapeutic interventions should be monitored more frequently, thus reducing the delay before repeating measurements (38) to a day or two.

Although a particular embodiment of the invention has been described in detail for purposes of illustration, various modifications may be made without departing from the spirit and scope of the invention. Accordingly, the invention is not to be limited, except as by the appended claims.

I claim:

1. A process for monitoring patients with chronic congestive heart failure, comprising the steps of:
    applying electrodes to two limbs of a patient;
    passing a high frequency current between the electrodes;
    measuring the current (I), voltage (V) and phase angle ($\phi$) between the voltage (V) and the measured current (I);
    calculating congestive heart failure (CHF) indicia values based on the measured current (I), voltage (V) and phase angle ($\phi$); and
    comparing the calculated CHF indicia values with baseline values to determine if differences therebetween are within established tolerances.

2. The process of claim 1, including the step of establishing the baseline values when the patient is in a known, stable condition.

3. The process of claim 2, including the step of initiating intervention when, during the comparing step, the differences between the calculated CHF indicia values and the baseline values are outside of established tolerances.

4. The process of claim 3, including the step of repeating the process for monitoring patients with chronic congestive heart failure at an interval determined by whether or not intervention was required.

5. The process of claim 3, wherein the calculated CHF indicia values include resistance (R) and reactance ($Z_c$).

6. The process of claim 5, wherein the calculated CHF indicia values include impedance (Z).

7. The process of claim 6, wherein a decrease in the phase angle ($\phi$) or any of the calculated CHF indicia values of resistance (R), reactance ($Z_c$) or impedance (Z), is an indicator of the need to initiate intervention.

8. The process of claim 7, wherein the tolerances from baseline values for the calculated CHF indicia values are on the order of five percent (5%) for resistance (R) and impedance (Z), ten percent (10%) for reactance ($Z_c$), and twenty percent (20%) for phase angle ($\phi$).

9. The process of claim 5, wherein the calculated CHF indicia values include total body water (TBW) and extracellular water (ECW).

10. The process of claim 9, wherein total body water (TBW) is calculated utilizing the formula:

$$TBW = 0.377 \ Ht^2/R + 0.14 \ Wt - 0.08 \ Age + 2.9 \ Gender + 4.65 \ \text{(Where Gender=1 for male and 0 for female)}, \text{ and}$$

wherein extracellular water (ECW) is calculated utilizing the formula:

$$ECW = 0.189 \ Ht^2/R + 0.52 \ Wt - 0.0002 \ Ht^2/Z_c + 1.03,$$

wherein Ht=the height of the patient and Wt=the weight of the patient.

11. The process of claim 9, wherein an increase in the calculated total body water (TBW) or extracellular water (ECW) is an indicator of the need to initiate intervention.

12. The process of claim 11, wherein the tolerances from baseline values for the calculated CHF indicia values are on the order of five percent (5%) for total body water (TBW) and extracellular water (ECW).

13. The process of claim 5, wherein the calculated CHF indicia values include a figure of merit indicative of the hydration status of the patient.

14. The process of claim 13, wherein the figure of merit is derived from the ratio of extracellular water (ECW) over fat-free mass (FFM).

15. The process of claim 14, wherein extracellular water (ECW) is calculated using the formula:

$$ECW = 0.189 \ Ht^2/R + 0.52 \ Wt - 0.0002 Ht^2/Z_c + 1.03, \text{ and}$$

wherein fat-free mass (FFM) is calculated utilizing the formula:

$$FFM = -15.26 - 0.775(Ht^2/R) + 0.146 \ Wt + 0.185 \ Z_c,$$

wherein Ht=the height of the patient and Wt=the weight of the patient.

16. The process of claim 14, wherein intervention is indicated when the ratio of extracellular water (ECW) to fat-free mass (FFM) is greater than approximately 0.30.

17. The process of claim 14, wherein an increase in the figure of merit on the order of one percent (1%) is an indicator of the need to initiate intervention.

18. A process for monitoring patients with chronic congestive heart failure, comprising the steps of:
    applying electrodes to two points on the body of a patient;
    passing a current at one or more high frequencies between the electrodes;
    measuring the current (I) and voltage (V) at each frequency;
    calculating congestive heart failure (CHF) indicia values based on the measured current(s) (I) and voltage(s) (V); and
    comparing the calculated CHF indicia values with baseline values to determine if differences therebetween are within established tolerances.

19. The process of claim 18, including the steps of establishing baseline values determined when the patient is in a known, stable condition, initiating intervention when, during the comparing step, the differences between the calculated CHF indicia values and the baseline values are outside of established tolerances, and repeating the process for monitoring patients with chronic congestive heart failure at an interval determined by whether or not intervention was required.

20. The process of claim 19, wherein the calculated CHF indicia values include total body water (TBW) and extracellular water (ECW), and wherein an increase in the calculated total body water (TBW) or extracellular water (ECW) is an indicator of the need to initiate intervention.

21. The process of claim 20, wherein the tolerances from baseline values for the calculated CHF indicia values are on the order of five percent (5%) for total body water (TBW) and extracellular water (ECW).

22. The process of claim 20, wherein the calculated CHF indicia values include a figure of merit, derived from the ratio of extracellular water (ECW) over fat-free mass (FFM), that is indicative of the hydration status of the patient.

23. The process of claim 22, wherein intervention is indicated when the ratio of extracellular water (ECW) to fat-free mass (FFM) is greater than approximately 0.30, or there is an increase in the figure of merit on the order of one percent (1%).

24. The process of claim 19, including the step of measuring the phase angle ($\phi$) between the measured current (I) and voltage (V) at each frequency, and wherein the calculated CHF indicia values include resistance (R), reactance ($Z_c$), and impedance (Z).

25. The process of claim 24, wherein a decrease in the phase angle ($\phi$) or any of the calculated CHF indicia values of resistance (R), reactance ($Z_c$) or impedance (Z), is an indicator of the need to initiate intervention.

26. The process of claim 24, wherein the tolerances from baseline values for the calculated CHF indicia values are on the order of five percent (5%) for resistance (R) and impedance (Z), ten percent (10%) for reactance ($Z_c$), and twenty percent (20%) for phase angle ($\phi$).

27. A process for monitoring patients with chronic congestive heart failure, comprising the steps of:

applying electrodes to two limbs of a patient;

passing a high frequency current between the electrodes;

measuring the current (I), voltage (V) and phase angle ($\phi$) between the voltage (V) and the measured current (I);

calculating congestive heart failure (CHF) indicia values, including resistance (R) and reactance ($Z_c$), based on the measured current (I), voltage (V) and phase angle ($\phi$);

comparing the calculated CHF indicia values with baseline values to determine if differences therebetween are within established tolerances;

initiating intervention when, during the comparing step, the differences between the calculated CHF indicia values and the baseline values are outside of established tolerances; and repeating the process for monitoring patients with chronic congestive heart failure at an interval determined by whether or not intervention was required.

28. The process of claim 27, including the step of establishing the baseline values when the patient is in a known, stable condition.

29. The process of claim 28, wherein the calculated CHF indicia values include impedance (Z), and wherein a decrease in the phase angle ($\phi$) or any of the calculated CHF indicia values of resistance (R), reactance ($Z_c$) or impedance (Z), is an indicator of the need to initiate intervention.

30. The process of claim 29, wherein the tolerances from baseline values for the calculated CHF indicia values are on the order of five percent (5%) for resistance (R) and impedance (Z), ten percent (10%) for reactance ($Z_c$), and twenty percent (20%) for phase angle ($\phi$).

31. The process of claim 27, wherein the calculated CHF indicia values include total body water (TBW) and extracellular water (ECW), and wherein an increase in the calculated total body water (TBW) or extracellular water (ECW) is an indicator of the need to initiate intervention.

32. The process of claim 31, wherein total body water (TBW) is calculated utilizing the formula:

$$TBW = 0.377\ Ht^2/R + 0.14\ Wt - 0.08\ Age + 2.9\ Gender + 4.65\ \text{(Where Gender=1 for male and 0 for female), and}$$

wherein extracellular water (ECW) is calculated utilizing the formula:

$$ECW = 0.189\ Ht^2/R + 0.52\ Wt - 0.0002\ Ht^2/Z_c + 1.03,$$

wherein Ht=the height of the patient and Wt=the weight of the patient.

33. The process of claim 31, wherein the tolerances from baseline values for the calculated CHF indicia values are on the order of five percent (5%) for total body water (TBW) and extracellular water (ECW).

34. The process of claim 27, wherein the calculated CHF indicia values include a figure of merit indicative of the hydration status of the patient.

35. The process of claim 34, wherein the figure of merit is derived from the ratio of extracellular water (ECW) over fat-free mass (FFM), wherein intervention is indicated when the ratio of extracellular water (ECW) to fat-free mass (FFM) is greater than approximately 0.30, and wherein an increase in the figure of merit on the order of one percent (1%) is an indicator of the need to initiate intervention.

36. The process of claim 35, wherein extracellular water (ECW) is calculated using the formula:

$$ECW = 0.189\ Ht^2/R + 0.52\ Wt - 0.0002\ Ht^2/Z_c + 1.03,\ \text{and}$$

wherein fat-free mass (FFM) is calculated utilizing the formula:

$$FFM = -15.26 - 0.775\ (Ht^2/R) + 0.146\ Wt + 0.185\ Z_c,$$

wherein Ht=the height of the patient and Wt=the weight of the patient.

* * * * *